United States Patent [19]

Matsushima

[11] Patent Number: 5,707,621

[45] Date of Patent: Jan. 13, 1998

[54] SUPRESSION OF NEPHRITIS-INDUCED PROTEIN EXCRETION BY ANTI-IL-8

[75] Inventor: Kouji Matsushima, Ishikawa Prefecture, Japan

[73] Assignee: Chugai Pharmaceutical Co., Ltd., Tokyo, Japan

[21] Appl. No.: 299,156

[22] Filed: Aug. 31, 1994

[51] Int. Cl.$^6$ .................. A61K 39/395; C07K 16/00; C07K 16/18; C07K 16/24

[52] U.S. Cl. .................. 424/145.1; 424/130.1; 424/158.1; 424/133.1; 424/809; 530/387.1; 530/387.3; 530/388.1; 530/388.23; 435/325; 435/326; 435/328; 435/335

[58] Field of Search .................. 424/145.1, 152.1, 424/545, 130.1, 143.1, 158.1, 133.1, 809; 435/240.27, 69.1, 70.21, 172.3, 172.2, 325, 326, 328, 335; 530/387.1, 388.23, 388.1, 388.15, 387.3, 808

[56] References Cited

U.S. PATENT DOCUMENTS

| | | | |
|---|---|---|---|
| 4,766,126 | 8/1988 | Takami | 514/267 |
| 4,840,960 | 6/1989 | Sterzel et al. | 514/356 |

FOREIGN PATENT DOCUMENTS

| | | |
|---|---|---|
| 9007861 | 7/1990 | WIPO . |

OTHER PUBLICATIONS

Harada et al, International Immunology., vol. 5:681–690.
Kincaid–Smith, Kidney International 36:1108–1111, 1989.
Reech et al, Cell 50:667, 1987.
Broaddus, V.C. et al, J. Immunol, 152:2960–2967, Feb. 15, 1994.
Chun Tharapai, A. et al, J. Immunol, 152:1783–1789, Feb. 15, 1994.
"Clinical Nephrology 2nd edition", Classification of Renal Disease, 29–33 (1978).
Brown and Company Inc.: "A Handbook of Kidney Nomenclature and Methodology", 167–195, (1975).
Pusey, C.D. et al., Immunopathology of Glomerular and Interstitial Disease, Diseases of the Kidney, ed. by Schrier, R.W. et al., Little, Brown and Company, Boston/Toronto, 1827–1884 (1988).
Germuth, F.G. et al., A Comparative Histologic and Immunologic Study in Rabbits of Induced Hypersensitivity of the Serum Sickness Type, *J. Exp. Med.* (1953) 97:257–282.
Dixon, F.J. et al. Experimental Glomerulonephritis, *J. Exp. Med.* (1961) 113:899–920.
Fleuren, G.J. et al. Experimental Glomerulonephritis in the Rat Induced by Antibodies Directed against Tubular Antigens, *Lab. Invest.* (1978) 8:496–501.
Couser, W.G. et al. Experimental Glomerulonephritis in the Isolated Perfused Rat Kidney, *J. Clin. Invest.* (1978) 62:1275–1287.
Yoshimura, T. *Proc. Natl. Acad. Sci. USA* Purification of a Human Monocyte–derived Neutrophil Chemotactic Factor that has Peptide Sequence Similarity to Other Host Defense Cytokines (1987) 84:9233.

Peveri, P. et al. A Novel Neutrophil–activating Factor Produced By Human Mononuclear Phagocytes *J. Exp. Med.* (1988) 167:1547.
Ko, Y–C. et al. A Sensitive Enzyme–linked Immunosorbent Assay for Human Interleukin–8, *J. Immunol. Method* (1992) 149:1227–1235.
Herbert, C.A. et al. Interleukin–8: A Review, *Cancer Investigation* (1993) 11:743–750.
Matsushima, K. et al. Molecular Cloning of a Human Monocyte–derived Neutrophil Chemotactic Factor (MDNCF) and the Induction of MDNCF mRNA by Interleukin 1 and Tumor Necrosis Factor, *J. Exp. Med.* (1988) 167:1883–1893.
Abbot, F. et al. Interleukin–1β Stimulates Human Mesangial Cells to Synthesize and Release Interleukins–6 and –8, *Kidney Int.* (1991) 40:597–605.
Kusner, D.J. et al. Cytokine– and LPS–induced Synthesis of Interleukin–8 from Human Mesangial Cells, *Kidney Int.* (1991) 39:1240–1248.
Zoja, C. et al. Interleukin–1β and Tumor Necrosis Factor–α Induced Gene Expression and Production of Leukocyte Chemotactic Factors, Colony–stimulating Factors, and Interleukin–6 in Human Mesangial Cells, *Am. J. Pathol.* (1991) 138:991–1003.
Brown, Z. et al. Cytokine–activated Human Mesangial Cells Generate the Neutrophil Chemoattractant, Interleukin 8, *Kidney Int.* (1991) 40:86–90.
Harada, A., et al. Expression of Recombinant Rabbit IL–8 in *E. coli* and Establishment of the Essential Involvement of IL–8 in Recruiting Neutrophils into Lipopolysaccharide–induced Inflammatory Site of Rabbit Skin, *Int. Immunol.* (1993) 5:681–690.
Sekido, N. et al. Prevention of Lung Reperfusion Injury in Rabbits by a Monoclonal Antibody against Interleukin–8, *Nature* (1993) 365:654–657.
Matsushima, K. et al., "Pathophysiological roles of interleukin 8 in inflammatory diseases," XIIth International Congress of Nephrology, Abstract (1993) p. 9 (or 74).
Wada, T. et al., "Prevention of experimental immune complex glomerulonephritis by the administration of a specific antibody against interleukin–8", The Journal of the American Society of Nephrology (ASN Program & Abstracts) (1993) p. 640, 21P.
Hisada, Y. et al., "The elevated production of interleukin–8 in glomerular diseases," The Journal of the American Society of Nephrology (ASN Program & Abstracts) (1993) p. 679, 108P.

(List continued on next page.)

*Primary Examiner*—Susan A. Loring
*Attorney, Agent, or Firm*—Morrison & Foerster LLP

[57] ABSTRACT

A method for ameliorating at least one of the symptoms of nephritis is disclosed. Administration of antibodies or immunologically reactive fragments thereof which are immunoreactive with the IL-8 of the subject suppresses the elevated excretion of protein and infiltration of neutrophils associated with this condition.

8 Claims, 9 Drawing Sheets

OTHER PUBLICATIONS

Wada, T. et al., "Prevention of proteinuria by the administration of anti–interleukin 8 antibody in experimental acute immune complex–induced glomerulonephritis", The Journal of Experimental Medicine (1994) 180(3) 1135–1140.

Wada et al. Prevention of Protein Urea by Administration at a–IL8 A6 a Experimental Acute Immune Complex–Indirect Glomerulonerphitus J. Exp. Med. Sep. 1994 180:1135.

Ko et al. Asensitive Enzyme Line of Immunoabsorbent Assay for Human IL8 J. Immunol. Meth. 149:227, 1992.

Wada et al. Detection of urine IL8 in Glomerular Diseases Kid. Int. 46:455, 1994.

Ko et al. Elevated IL8 In Urine of Patients with UTI Infect. & Immun. Apr., 1993 61:1307.

Emery et al. Humanized mAbs for Therapeutic Applications Exp. Opin. Invest. Drugs 3:241 1994.

Cronstein et al. The Adhesion Molecules of Inflammation Arthr. & Rheum. 36:147 1993.

Cunningham & Harris AB Engineering–How to be Human TIBTECH Apr. 1992 10.

Goding Mabs: Principles & Puncture Academic Press 1986 259–290.

Production & Application of Mabs In Cell Biology, Biochem. & Immunol.

SUPPRESSION OF NEPHRITIS-INDUCED PROTEIN EXCRETION BY ANTI-IL-8

FIELD OF THE INVENTION

The present invention relates to the prevention and/or the treatment of nephritis. More particularly, the invention concerns a method of suppressing neutrophil infiltration and protein excretion associated with glomerulonephritis comprising administering an antibody directed against interleukin 8 (IL-8).

BACKGROUND ART

Nephritis

Renal disorders can be classified pathologically into vascular disease, glomerular disease, tubulointerstitial disease and renal failure by the clinical state based on the major lesion site. At present, detection of urinary protein, especially urinary albumin has been recognized as an important diagnostic criterion of these disorders (see, for example, "Clinical Nephrology 2nd edition", 29–33, 1978, vitro, Brown and Company Inc.: "A Handbook of Kidney Nomenclature and Methodology", 167–195, 1975, vitro, Brown and Company Inc.")

All renal disorders with glomerular dysfunction as the main lesion are accompanied by remarkable abnormalities in the urinary protein level and urinary precipitates. These are induced by inflammation in the glomeruli. Glomerulonephritis is characterized by the infiltration of inflammatory cells into glomeruli and proliferation of mesangial cells (Pusey, C. D. et al., Diseases of the Kidney, ed. by Schrier, R. W. et al., Little, Brown and Company, Boston/Toronto, 1827–1884 (1988). The inflammation in the glomeruli occurs via various mechanisms. In particular, it is considered that glomerulonephritis may be mediated by an immunological mechanism at the acute phase (Germuth, F. G. et al., J. Exp. Med. (1953) 97:257–282; Dixon, F. J. et al. J. Exp. Med. (1961) 113:899–920; Fleuren, G. J. et al. Lab. Invest. (1978) 8:496–501; and Couser, W. G. et al. J. Clin. Invest. (1978) 62:1275–1287). This immunological mechanism involves two pathways; one is characterized by the deposition of immune complexes which have been preformed in circulating blood to the glomeruli and the other by the binding of a circulating antibody to an antigen which is on the surface of cells constituting the glomeruli. The deposition of immune complexes in the glomeruli by either mechanism induces the activation of the complement system and the infiltration of inflammatory cells including monocytes and neutrophils, and then glomerulus tissues are destroyed.

In several experimental animal models of immune complex-mediated glomerulonephritis, the infiltration of leukocytes, in particular, neutrophils is frequently observed at the site of the main lesion, in the early stage of the disease. The precise mechanism and the pathological role of the infiltration of leukocytes remain unclear. However, as an inflammatory reaction appears to be involved, and steroids are commonly used in the treatment of glomerulonephritis. This approach to treatment appears less than ideal since steroids exhibit a variety of undesirable side effects, some of them serious.

Interleukin-8 (IL-8)

IL-8, formerly called monocyte-derived neutrophil chemotactic factor (MDNCF) (Yoshimura, T. Proc. Natl. Acad. Sci. USA (1987) 84:9233) or neutrophil attractant/activation protein-1 (NAP-1) (Peveri, P. et al. J. Exp. Med. (1988) 167:1547, is a chemotactic and activating polypeptide for human leukocytes (Ko, Y-C. et al. J. Immunol. Method (1992) 149:1227–1235). IL-8 is a potent neutrophil chemotactic cytokine and participates in the migration of neutrophils toward inflammatory sites. IL-8 activates neutrophils by accelerating degranulation and elevating the free $Ca^{2+}$ concentration in the cytoplasm and also induces neutrophil migration (Hebert, C. A. et al. Cancer Investigation (1993) 11:743–750) to thereby destroy the infiltrated tissue. IL-8 is secreted by mesangial cells and endothelial cells in response to IL-1 or TNFα in vitro (Matsushima, K. et al. J. Exp. Med. (1988) 167:1883–1893; Abbot, F. et al. Kidney Int. (1991) 40:597–605; Kusner, D. J. et al. Kidney Int. (1991) 39:1240–1248; Zoja, C. et al. Am. J. Pathol. (1991) 138:991–1003; and Brown, Z. et al. Kidney Int. (1991) 40:86–90). Differential cleavage of the secreted IL-8 at N-terminus yields variants including the 79-, 77-, 72-, 71-, 70- and 69-amino acid forms. The relative proportion of IL-8 variants secreted depends on both the type of cell and the type of stimulus used (Hebert, C. A. et al. (supra).

The present inventor has found that in several recognized animal models, the administration of WS-4 antibody, which specifically neutralizes the biological activities of IL-8 by binding to IL-8, suppresses infiltration of neutrophils, and inhibits the neutrophil-dependent inflammatory reaction in LPS-induced dermatitis (Harada, A., et al. Int. Immunol. (1993) 5:681–690) and lung reperfusion injury (Sekido, N. et al. Nature (1993) 365:654–657). However, it remains unknown whether IL-8 is involved in nephritis.

DISCLOSURE OF THE INVENTION

The invention provides a new approach to preventing and/or treating nephritis. This approach is grounded in the inventor's hypothesis that IL-8 participates in neutrophil infiltration in glomerulonephritis and is responsible for elevated levels of protein excreted in the urine. The present inventor has verified this hypothesis in animal models and shown that administration of an antibody directed against IL-8 lower the levels of excretion of protein and albumin to normal as well as suppresses in part neutrophil infiltration into the glomeruli.

Thus, in one aspect, the invention is directed to a method to decrease the excretion of protein and/or albumin into the urine of a subject afflicted with nephritis, which method comprises administering to said subject antibodies immunoreactive with the IL-8 of the subject. Alternatively, or in addition, other moieties that interfere with the biological activity of IL-8 could be used. Similarly, the invention is directed to a method to suppress neutrophil infiltration of the glomeruli, which method comprises administering to said subjects antibodies immunoreactive with the IL-8 of the subject, or other moieties that interfere with IL-8. Immunoreactive fragments of the antibody may also be used. The methods of the invention may be combined with other treatments for nephritis.

In another aspect, the invention is directed to pharmaceutical compositions useful in the methods of the invention.

The invention method is thus useful in ameliorating at least one of the symptoms of nephritis, particularly glomerulonephritis, and more particularly inflammatory glomerulonephritis such as glomerulonephritis caused by the deposition of immune complexes or glomerulonephritis accompanied by the infiltration of neutrophils into the glomeruli.

MODES OF CARRYING OUT THE INVENTION

Figure 1A:
FIGS. 1a, 1b and 1c are copies of photomicrographs (×3000 magnification) showing the results of a histological study on renal tissues of the BSA-immunized and control antibody-treated rabbit (FIG. 1a), BSA-immunized and anti-IL-8 antibody-treated rabbit (FIG. 1b) and normal rabbit (FIG. 1c).

The invention takes advantage of the discovery by the inventor herein that IL-8 appears to mediate the infiltration of neutrophils into the glomeruli in the progress of the inflammatory kidney condition known as nephritis. The methods of the invention, designed to ameliorate or prevent the symptoms associated with this condition, therefore employ substances which interfere with the biological activity of IL-8. One class of such materials consists of antibodies immunoreactive with the IL-8 secreted by the cells of the afflicted subject or immunologically reactive fragments thereof. Certain IL-8 analogs containing amino acid substitutions or truncations at the N-terminus are IL-8 antagonists and also interfere with IL-8 activity. Moser, B. et al. *J Biol Chem* (1993) 268:7125–7128.

The antibodies, or immunologically reactive fragments, can be prepared in a variety of ways, as is generally known in the art. In general, such antibodies may be prepared by immunizing a suitable subject with IL-8 and monitoring the titers of IL-8 in the blood of the immunized animal. The antisera can be used directly optionally preceded by purification of the antibodies, or monoclonal antibodies may be prepared from the antibody-secreting B cells of the immunized animal using art-recognized methods.

While the IL-8 used for immunization is generally the IL-8 secreted by the species of which the subject to be treated is a member, it is not necessary that this be the case as long as antibodies raised against the injected IL-8 are cross-reactive with the IL-8 of the subject. For example, in the animal model illustrated below, antibodies raised against human IL-8 were shown to be immunoreactive with rabbit IL-8. Thus, the IL-8 used for immunization need only have the capacity to generate antibodies which are immunoreactive with the IL-8 of the subject to be treated.

In addition, recombinant methods for production of antibodies are known, and the antibodies useful in the invention can be prepared accordingly. In general, this could be approached by isolating DNA from immortalized B cells secreting the desired anti-IL-8 and using the relevant DNA for constructing suitable expression systems for production of these antibodies recombinantly.

In all of the foregoing cases, the antibodies may be treated to prepare only the immunologically reactive portions thereof, or the recombinant production systems may be designed to produce these fragments. The substitution of immunologically reactive fragments for whole antibodies, such as the Fab, Fab', F(ab')$_2$, Fv, (or single-chain Fv portions having the H and L chain linked) is well known. See, for example, Byrd, et al. *TIBTECH* (1991) 132–137.

The antibodies or fragments useful in the method of the invention thus specifically bind to the IL-8 of the subject to be treated and inhibit the binding of such IL-8 to neutrophils. The antibodies can be produced in hosts other than those of the species of the subject to be treated and, indeed, this is commonly the case. For example, for treatment of humans, either human monoclonal antibodies or monoclonal antibodies derived from other sources such as mice can be used.. Exemplified herein is WS-4 described by Ko, Y. et al. *J. Immunol. Meth.* (1992) 149:1227–1235. WS-4 is an antibody secreted by hybridomas prepared from B cells of mice immunized with human IL-8 and is of the IgGIκ type. It has the ability to neutralize biological activities of human IL-8 by specifically binding thereto and by inhibiting the binding of human IL-8 to neutrophils.

Additional examples of such antibodies neutralizing the biological activities of IL-8 include antibody DM/C7 (Mulligan, M. S. et al. *J. Immunology* (1993) 150:5585–5595); antibody A5.12.14 (Boylan, A. M. et al. *J Clin Invest* (1992) 89:1257) and anti-Pep-1 antibody and anti-Pep-3 antibody disclosed in International Patent Application WO 92/04372.

Preparation of Anti-IL-8

By way of illustration, the anti-IL-8 for use in the method of the invention, when humans are the subjects, can be prepared by immunizing an animal, e.g., a mouse, rabbit or guinea pig, with IL-8 from humans or other appropriate species, recovering B cells, performing cell fusion, and isolating and cloning the resulting hybridomas producing the anti-IL-8 monoclonal antibody using standard methods.

Human IL-8, including IL-8 variants, (Matsushima, K. et al. *J. Exp. Med.* (1988) 167:1883–1893; Yoshimura, T. et al. *Mol. Immunol.* (1989) 26:87–93; Van Damme, J. et al. *Eur. J. Biochem.* (1989) 181:337–344) can, for example, be used as the sensitizing antigen. Immunization is generally conducted by intraperitoneal injection, preferably with the antigen diluted or suspended in PBS or a physiological saline, and administered with a suitable amount of a standard adjuvant several times, at intervals of 4 to 21 days until the desired antibody is detected in serum of the immunized animal. Spleen cells are preferably used as the immunocytes.

Various known cell lines such as P3 (P03X63Ag8. 653) (*J. Immunol.* (1978) 123:1548), pE-U1 (*Current Topics in Microbiology and Immunology* (1978) 81:17, NS-1 (*Eur. J. Immunol.* (1976) 6:511–519), MPC-11 (*Cell* (1976) 8:405–415), SP2/0 (*Nature* (1978) 276:269–270), FO (*J. Immunol.* (1980) 35:1–21), S194 (*J. Exp. Med.* (1978) 148:313–323) and R210 (*Nature* (1979) 277:131–133) may be suitably employed as the immortalizing myeloma cells to be fused with the immunocytes.

The cell fusion of the above-mentioned immunocytes with the myeloma cells can be carried out in accordance with standard methods, for example, the method of Milstein et al. (*Methods Enzymol.* (1981) 73:3–46).

Cell fusion is performed in a standard nutrient medium, for example, RPMI-1640 medium or MEM, optionally with a serum replenisher, such as fetal calf serum (FCS) as a supplement, in the presence of a facilitator of cell fusion such as polyethylene glycol (PEG) or Sendai virus (HVJ). If required, a reagent such as dimethyl sulfoxide may be used to elevate the fusion efficiency. A 1-to-10 ratio of immunocytes to myeloma cells is preferred.

In one illustrative protocol, the immunocytes are mixed with the myeloma cells in the medium supplemented with a PEG (MW 1000–6,000) solution, which has been preheated to about 37° C. and added to the medium at a concentration of about 30 to 60% (w/v). Medium is successively added, the obtained mixture is centrifuged and the supernatant is removed. After repeating this procedure, the desired hybridomas can be obtained.

Successful fusions can be selected by incubation in a standard selection medium, such as HAT (hypoxanthine, aminopterin and thymidine) medium for a time sufficient to remove unfused cells, usually several days to several weeks. Individual colonies are obtained by dilution and cloning.

Hybridomas capable of producing the desired antibody are screened in accordance with the conventional limiting dilution analysis, followed by cloning of successful hybridomas. Antibody which neutralizes the biological activities of IL-8 of the species to be treated can be screened for use in binding inhibition bioassay to human neutrophils as described in Schroeder, J.-M. et al. *J. Immunol* (1987) 139:3474–3483. The selected hybridoma clone is cultured in vitro or in mammalian hosts and recovered from the culture or from the ascites fluid, respectively. The immunoglobulins are then purified using standard purification techniques and, if desired, immunologically reactive fragments prepared.

The desired hybridomas can be stored in liquid nitrogen.

The availability of recombinant techniques for antibody production permits monoclonal antibodies which have been artificially modified to minimize the immunogenicity against humans to be used, such as a chimeric antibody consisting of the variable region of a monoclonal antibody of a nonhuman mammal, such as a mouse, and the constant region of a human antibody. A reshaped human antibody useful in the present invention can also be obtained using the method described in International Patent Application No. WO 92/19759. If necessary, amino acids in the framework region (FR) of the variable regions may be replaced in such a manner that the complementarity determining regions of the reshaped human antibody can form the proper antigen binding site (Sato, K. et al. *Cancer Res* (1993) 53:851–856).

Mode of Administration

The administration of substances which interfere with the functioning of IL-8 have been demonstrated to suppress the infiltration of neutrophils into the glomeruli and to lower the levels of excretion of protein and albumin in urine to normal in subjects that are afflicted with nephritis. Accordingly, these substances may be used to exert these effects in such subjects.

The subjects may be any animal subject having a condition of nephritis, in particular, glomerulonephritis, and more particularly of glomerularnephritis where deposition of antibody or an immune complex in the renal tissue can be observed. Enhanced susceptibility of the subjects to this treatment can therefore be assessed by assaying the glomeruli for such immune complexes or antibody by biopsy and immunohistochemical observation. However, the treatment is effective even in the absence of antibody or immune complexes in renal tissue. Animals subject to these conditions include humans, primates, domestic animals, livestock, and domestic fowl. Cross reactivity with particular antibodies not raised with respect to the IL-8 of the subject permits use of the raised antibodies in animals that have homologs of IL-8 from the subject. For example, antibodies to human IL-8 are immunoreactive with IL-8 of sheep, pig, rabbit and guinea pig.

For humans, the following disorders are representative: acute nephritis syndrome, in particular, poststreptococcal glomerulonephritis which occurs following infection with *Streptococcus pyogenes* and acute glomerulonephritis accompanying bacterial infections other than hemolytic streptococcus; rapidly progressive glomerulonephritis and nephritis accompanying Goodpasture's Syndrome (and showing similar symptoms thereto), IgA nephropathy, and nephritis accompanying Schoenlein-Henoch's purpura (and showing similar symptoms thereto); lupus nephritis caused by systemic lupus erythematosus which is a typical immune complex disease and nephritis accompanying progressive systemic sclerosis and showing similar symptoms; nephritis accompanying polyarteritis nodosa; nephritis accompanying Wegener's granulomatosis, idiopathic membranous glomerulopathy, membranoproliferative glomerulonephritis, interstitial nephritis, in particular, acute interstitial nephritis showing remarkable cell infiltration; nephritis accompanying serum sickness; and nephritis accompanying cryoglobulinemia.

The anti-IL-8 may be administered, preferably, by parenteral injection, for example, via intravenous, intramuscular, intraperitoneal, or subcutaneous injection, in a dosage range for humans of 1 to 1000 mg depending on the condition and age of the patient. This amounts to roughly 10 µg/kg–50 mg/kg of body weight for animals in general. Of course, optimization of dosage and of administration protocols for a particular species and for a particular subject are routine.

The anti-IL-8 may be formulated in a conventional manner as described in *Remington's Pharmaceutical Sciences*, latest edition, Mack Publishing Company, Easton, Pa. For example, a preparation for injection may be obtained by dissolving purified anti-IL-8 in a solvent such as a physiological saline or a buffer solution and then adding a substance such as Tween 80, gelatin or human serum albumin, to the solution to prevent nonspecific adsorption by the surfaces of the vessel containing the preparation. The preparation may be freeze-dried and reconstituted prior to use. Mannitol or glucose may be used as a filler for freeze-drying. The formulations may optionally also include additional active substances useful in the treatment of nephritis.

Development of a Rabbit Inflammatory Glomerulonephritis Model

Effects of the administration of anti-IL-8 for the treatment of nephritis can be experimentally tested in animal models such as rabbits. A rabbit model recognized to be predictive of the effects of various treatments in humans has been developed. Rabbits are immunized with an antigen, for example, bovine serum albumin (BSA) to stimulate the animals to produce an antibody, then a large amount of BSA is administered to form an antigen (BSA)/antibody complex (immune complex), causing the animals to develop immune complex-mediated glomerulonephritis.

Test substance, such as anti-IL-8 or a control substance is also administered in accordance with the protocol. Various parameters including 1) the deposition of the antibody or the immune complex into glomerulus, 2) infiltrating neutrophil count in glomerulus and 3) changes in urinary protein level and urinary albumin level can be determined and compared between animals administered test substance and those administered control.

PREPARATION A

Preparation of Hybridomas and Anti-IL-8

Hybridomas producing the antihuman IL-8 antibody WS-4 were prepared by fusing spleen cells of a BALB/C mouse immunized with human IL-8 with mouse myeloma cells P3X63-Ag8.653 by a conventional method with polyethylene glycol.

After screening by using the biological neutralization activity of human IL-8 as an indicator, the hybridoma WS-4 was established (Ko, Y. et al. (supra)).

Typing performed by using a mouse monoclonal antibody isotyping kit (Amersham International plc) showed WS-4 had κ type L-chain and γ1 type H-chain. In addition to recognizing human IL-8, WS-4 also recognizes rabbit IL-8.

The following example is intended to illustrate but not to limit the invention.

The murine hybridoma designated "WS-4" which produces the WS-4 monoclonal antibody was deposited at the Bioengineering Industrial Technology Research Institute of the Agency of Industrial Science and Technology (1-1-3 Higashi, Tsukuba, Ibarald, Japan) on Apr. 17, 1996, with the identifier "FERM BP-5507" under the terms of the Budapest Convention.

EXAMPLE 1

Japanese White rabbits weighing 2 kg (purchased from Sankyo Labo Service, Inc.) were quarantined for 1 week to confirm the absence of any disease before use. On day 0, each rabbit was immunized subcutaneously with 4 mg/kg body weight of crystallized bovine serum albumin (BSA) (Wako Pure Chemical Industries, Ltd.). The BSA was dissolved at 2 mg/ml in physiological saline and the solution mixed with an equal volume of complete Freund's adjuvant (CFA; Iatron). On day 7, each rabbit was subjected to a single intravenous (IV) injection of a mixture of both 500 mg of BSA with 10 µg of *E. coli* (*Escherichia coli* O55:B55) lipopolysaccharide (LPS; Difco Laboratories, Detroit, Mich.) dissolved in 2 ml of physiological saline. On day 8, 10 µg of LPS dissolved in 1 ml of physiological saline was injected IV. This protocol induces antigen (BSA)/antibody complex (immune complex)-mediated inflammatory glomerulonephritis in the rabbits.

10 mg of antihuman IL-8 antibody WS-4 (IgG1 κ type), prepared in Preparation A, was dissolved in 1 ml of physiological saline and intravenously injected into 10 test rabbits simultaneously with the BSA and LPS injection on day 7 referenced above and again with the LPS injection on day 8.

Mouse monoclonal antibody TpM-1 (IgG1 κ type), which recognizes a constituent of *Toxoplasma gondii* (Ogata, K. et al. *J. Immunol. Methods* (1983) 65:75–82) was injected into 9 control rabbits on days 7 and 8 in the same manner as anti IL-8.

Four hours after the administration of WS-4 or control antibody on day 8, the rabbits were sacrificed for histological and immunohistological examination of the renal tissues.

(1) Histological Findings

A part of the renal tissue obtained from each rabbit was fixed in 10% buffered formalin, embedded in paraffin, cut into 4 µm sections and stained with a periodic acid Schiff (PAS) reagent. These sections were observed under light microscope and then the severity and the range of glomerular lesions were evaluated by two criteria: 1) hypercellularity of cells constituting the glomeruli and 2) extent of infiltration of polymorphonuclear leukocytes (PMN) into the glomeruli.

Figure 1B:
Figure 1C:
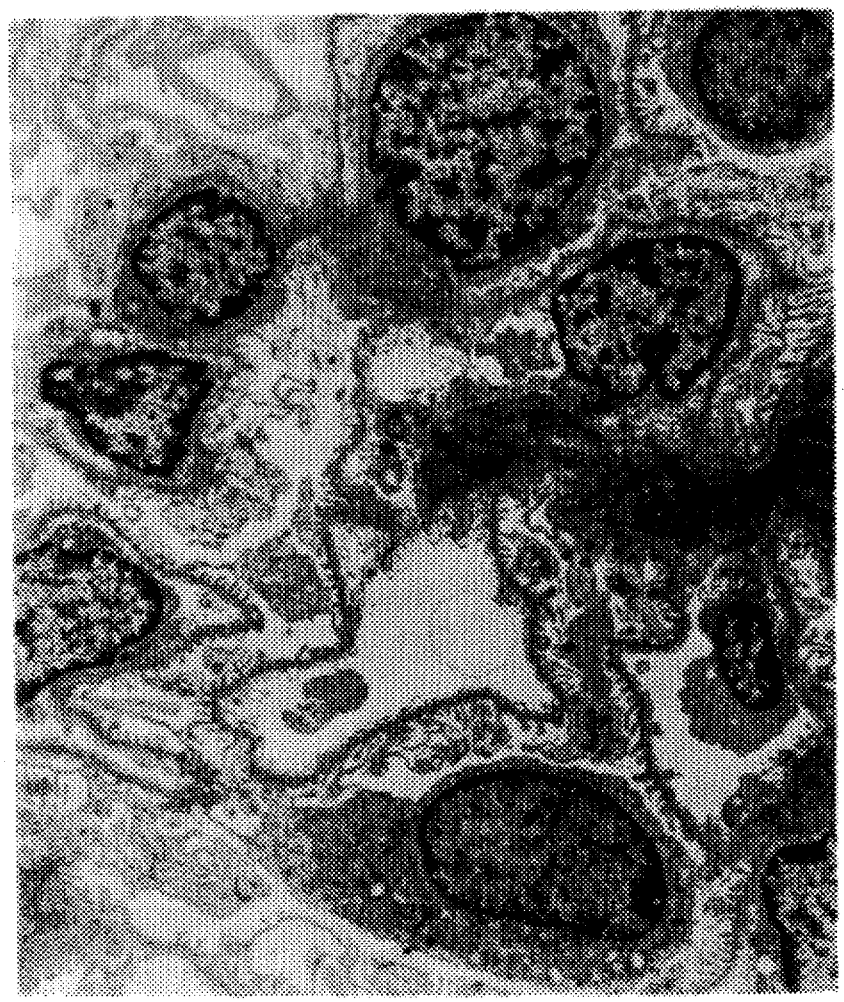

The results are shown in FIGS. 1a–1c.

Hypercellularity: both the test group immunized with BSA and treated with WS4 (FIG. 1b) and controls immunized with BSA and treated with TPM-1 (FIG. 1a) showed little hypercellularity, similar to the results for normal, untreated rabbits (FIG. 1c). However, while the controls showed fused epithelial foot processes of the free wall of glomerular capillaries near the infiltrated leukocytes as indicated by the arrow in FIG. 1a, neither the untreated rabbits (FIG. 1c) nor the test group (immunized with BSA and treated with WS-4) (FIG. 1b) showed fusion of epithelial foot processes even if neutrophils accumulated in the glomerular capillaries (FIG. 1b).

Figure 2:
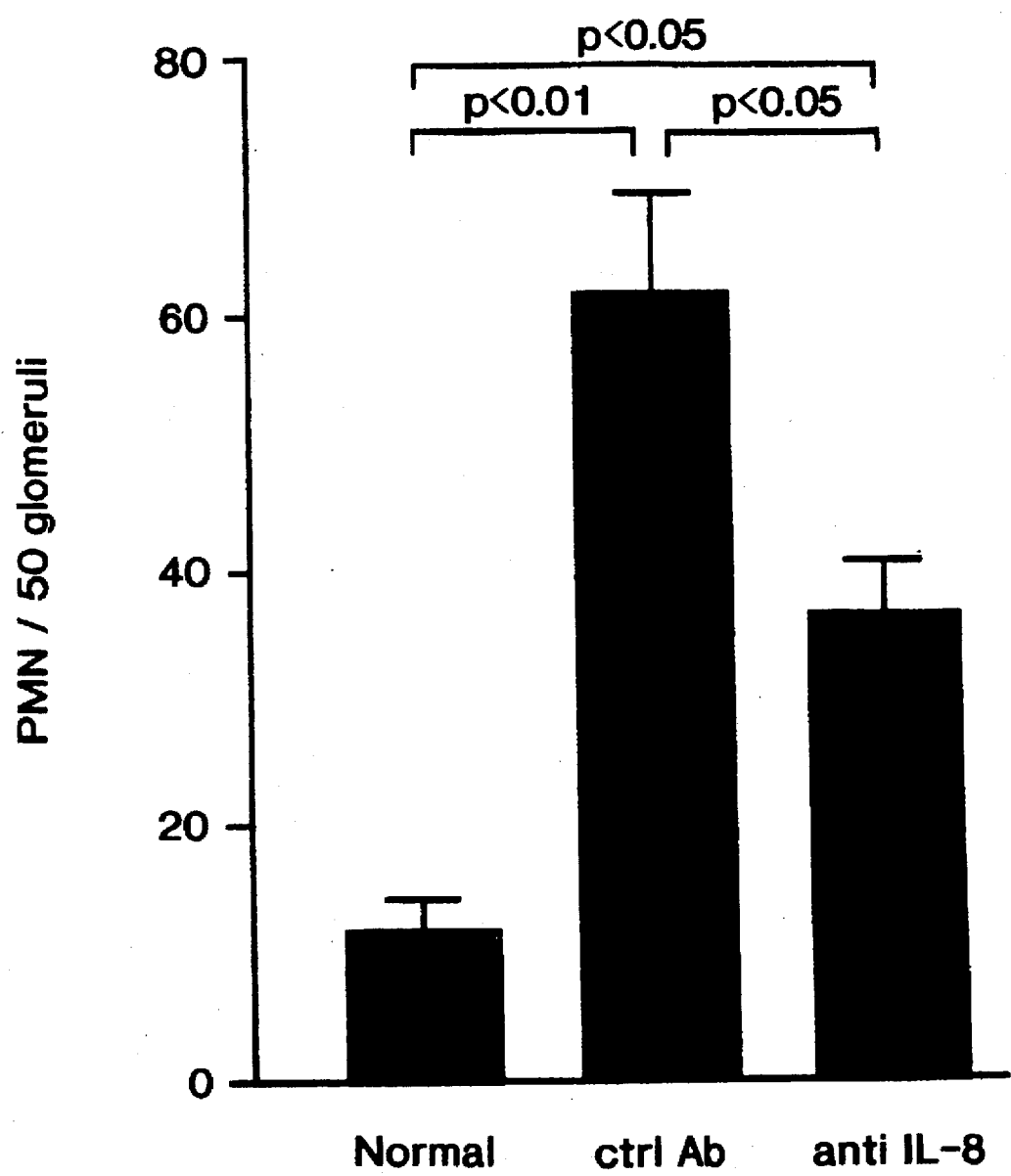
FIG. 2 is a bar graph showing suppression of infiltration of neutrophils into the glomeruli by anti-IL-8.

Infiltration of PMN: controls (immunized with BSA and treated with TPM-1) showed extensive infiltration of PMN into the glomeruli (FIG. 1a). PMN infiltration into the glomeruli was reduced by 40% in the animals treated with WS-4 (62.7±7.6 vs. 37.7±3.7) (See FIG. 2). Thus, anti-IL-8 suppresses PMN infiltration in inflammatory glomerulonephritis induced by deposition of the immune complex, suggesting that IL-8 participates in this migration.

(2) Effects of Antibody Administration on Deposition of Immune Complex

Parts of the rabbit renal tissues obtained above were rapidly frozen in n-hexane, cooled with a mixture of dry ice with acetone and then cut into 4 µm sections with a cryostat (of the Tissue-Tek II system; Miles, Naperville, Ill.). The sections were reacted with either fluorescein isothiocyanate (FITC)-conjugated antirabbit IgG antibody or anti-BSA antibody (Cappel Laboratories, Malvern, Pa.) in accordance with the fluorescent antibody method of Camussi, G. et al. (*Am. J. Pathol.* (1988) 131:418–434).

Figure 3A:
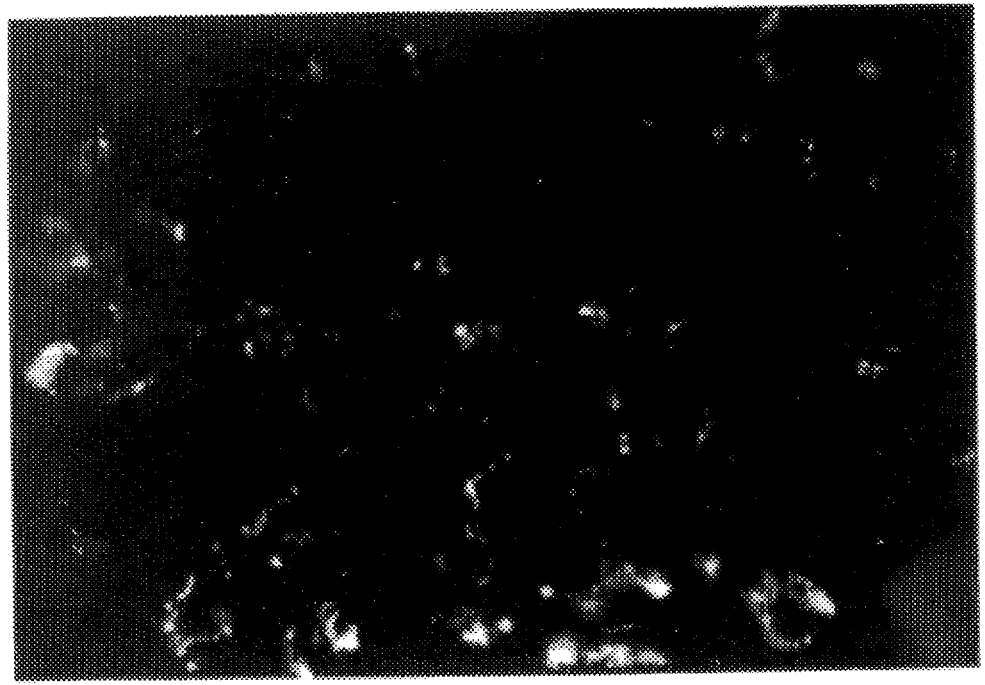
FIGS. 3a and 3b are copies of photomicrographs (×300 magnification) showing the results of immunohistological observation on renal tissues of the BSA-immunized, control antibody-treated rabbit wherein anti-BSA antibody (FIG. 3a) or anti-rabbit IgG antibody (FIG. 3b) was used as an antibody for detecting the deposition of BSA and rabbit IgG in glomeruli.
Figure 3B:
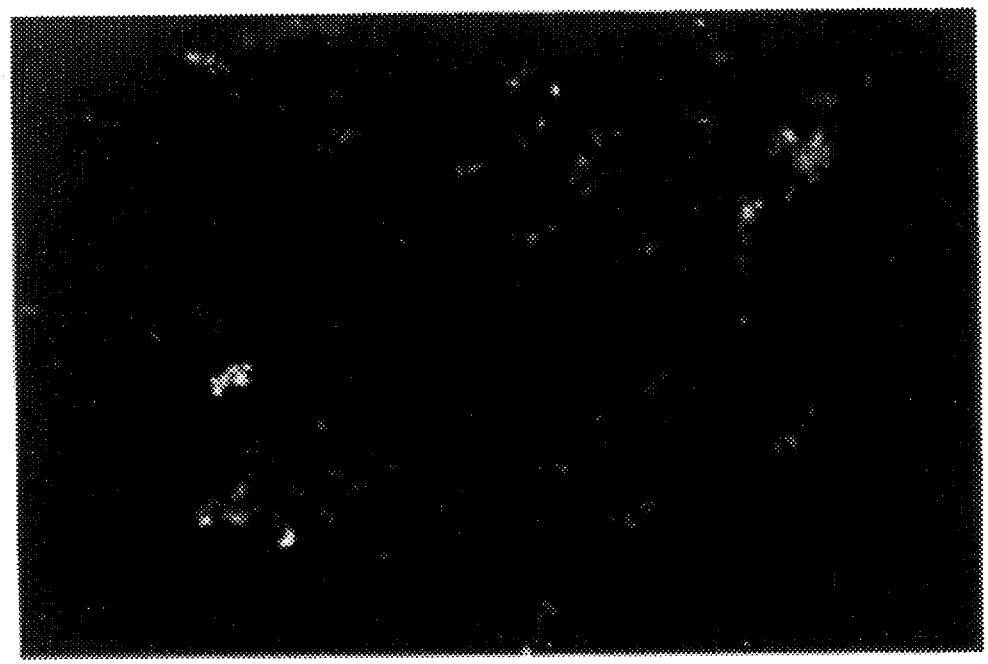
Figure 4:
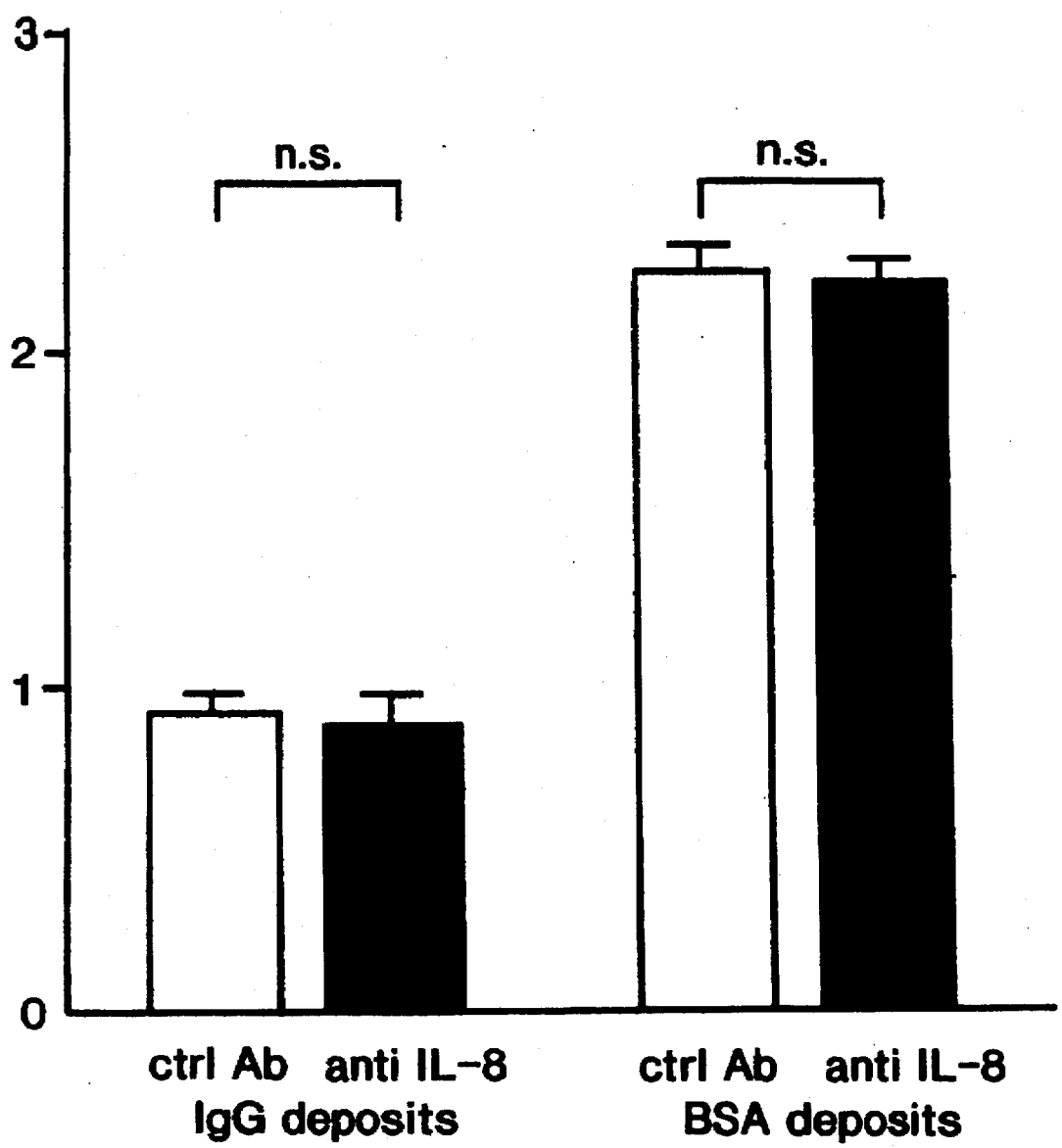
FIG. 4 is a bar graph showing the effect of anti-IL-8 on deposition of the immune complex.

The stained sections were observed under a fluorescence microscope. The amount and extent of fluorescence were evaluated in at least 50 glomeruli and were ranked in 4 grades of 0 to 3 (negative, scattered, weakly diffuse, strongly diffuse). The results are shown in FIGS. 3a, 3b and 4.

Both the control group treated with TPM-1 (FIGS. 3a and 3b) and the test group treated with WS-4 showed the deposition of BSA and rabbit IgG in the glomerulus. Semi-quantified evaluation of the deposition of BSA and rabbit IgG indicated that there was no significant difference between the two groups. Thus, anti-IL-8 does not appear to affect immune complex deposition in inflammatory glomerulonephritis.

(3) Detection of IL-8 Production and Excretion

Figure 5A:
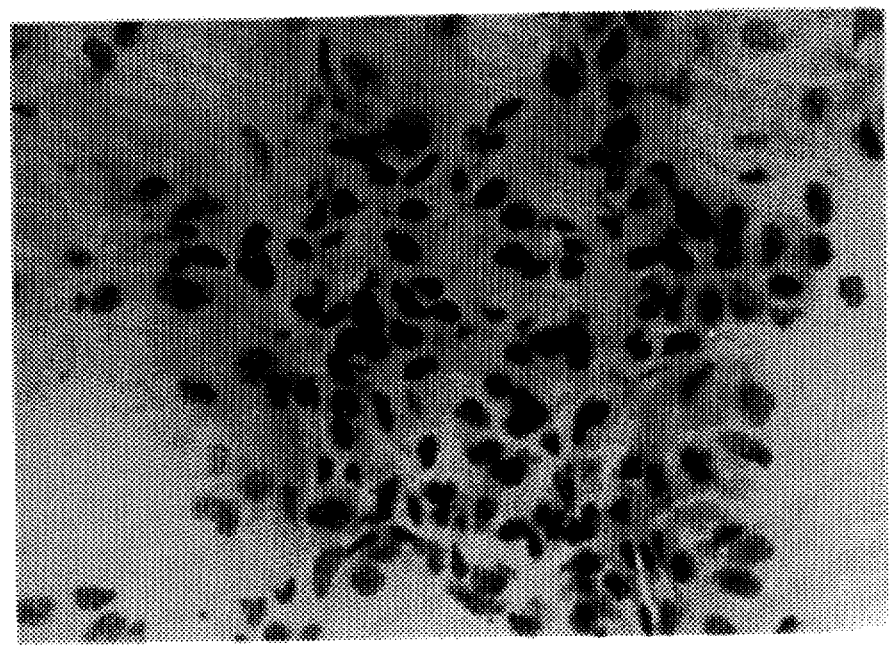
FIGS. 5a and 5b are copies of photomicrographs (×250 magnification) showing production of IL-8 protein in renal tissues by staining with WS-4 in untreated normal rabbit (FIG. 5a) and BSA-immunized rabbit (FIG. 5b).
Figure 5B:
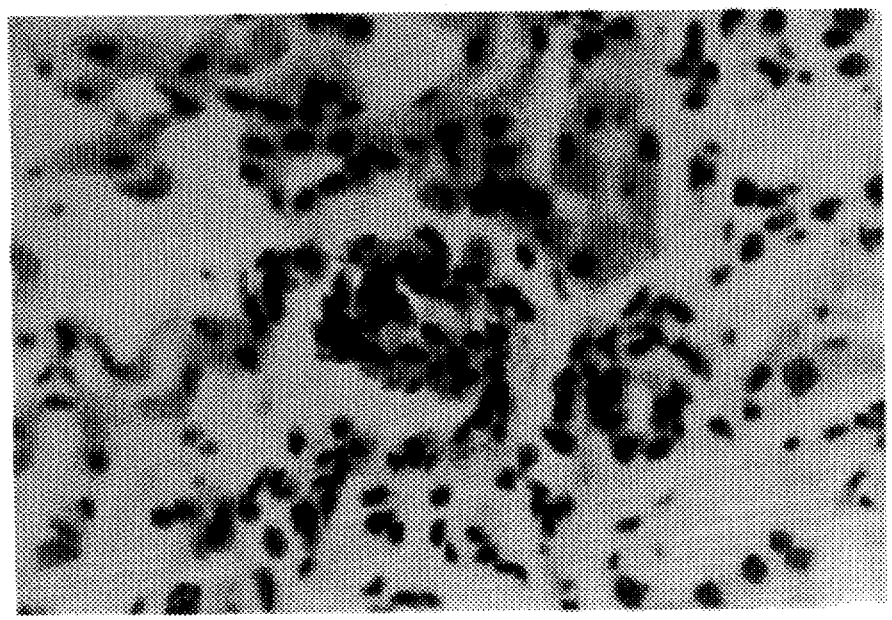

The production of IL-8 by the glomerular cells of rabbits with glomerulonephritis was assessed by direct immunohistochemical staining with avidin/biotin peroxidase and WS-4. IL-8 was detected in the glomerular mesangial cells, epithelial cells and monocytes in rabbits with nephritis induced as described above (FIG. 6), but not in normal rabbits (FIG. 5a).

Figure 6:
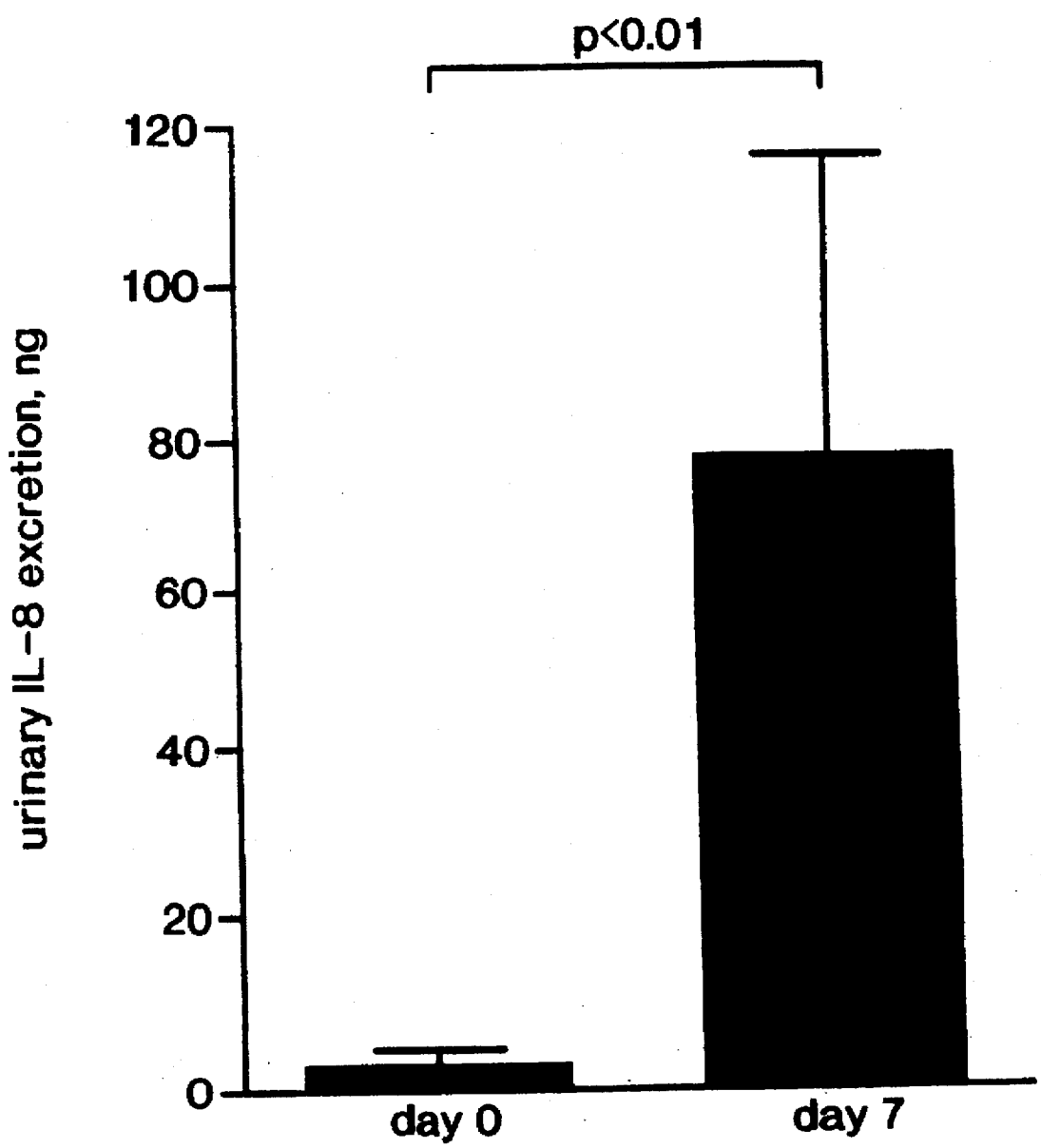
FIG. 6 is a bar graph showing urinary IL-8 excretion in BSA-immunized, control antibody-treated rabbits.
Figure 7:
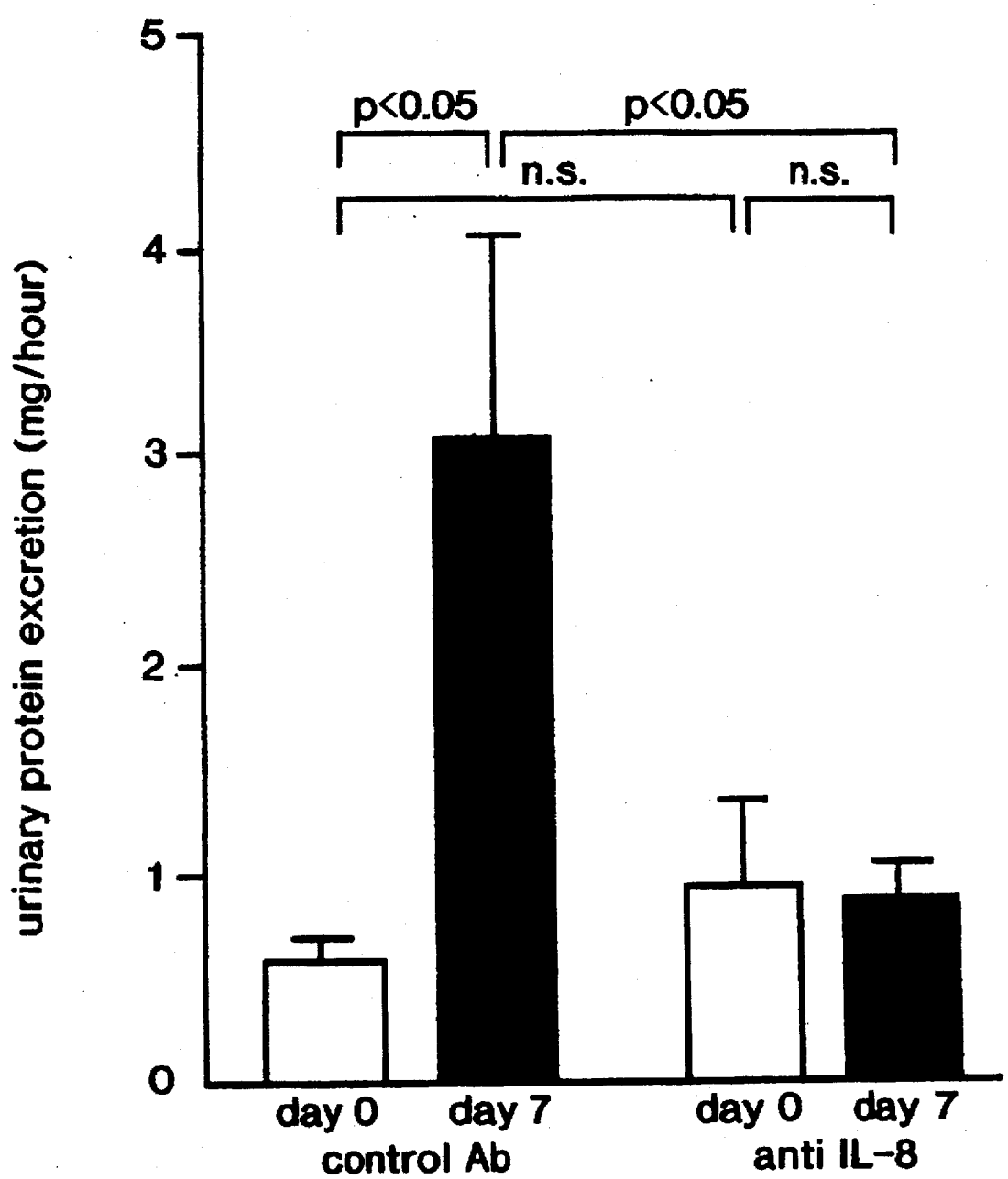
FIG. 7 is a bar graph showing the effect of anti-IL-8 on the urinary protein excretion.
Figure 8:
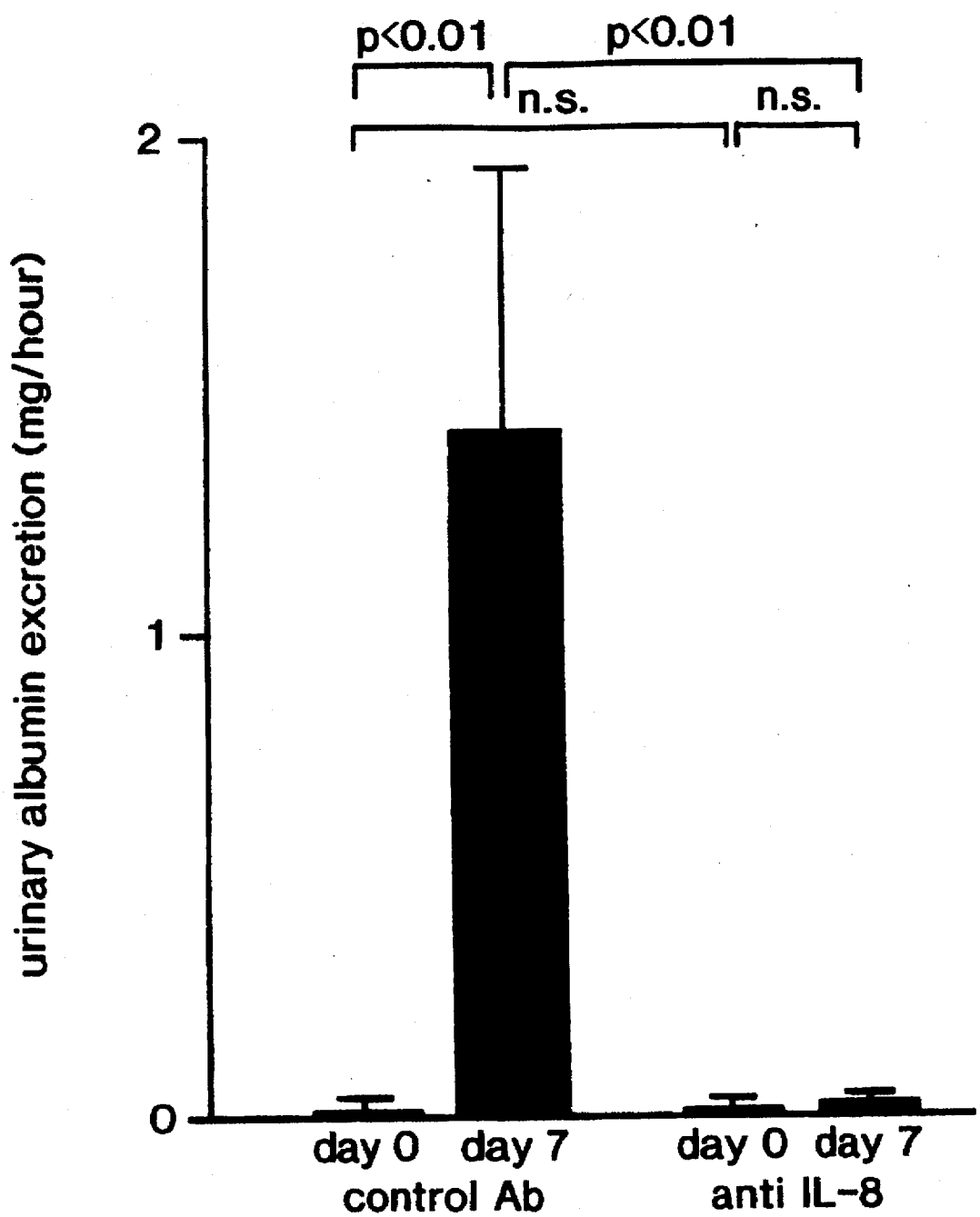
FIG. 8 is a bar graph showing the effect of anti-IL-8 on the urinary albumin excretion.

The excretion of IL-8 in urine of the rabbits with glomerulonephritis induced as described above was also assessed. Samples were collected using a metabolic cage during 24 hours until the BSA-immunization at day 0 and for 28 hours from day 7 to time of sacrifice. At day 7, urinary IL-8 excretion significantly increased compared to day 0 in the control group treated with TPM-1 (FIG. 6). No IL-8 was detected in the plasma.

This suggests IL-8 might be locally produced in the glomerulus in immune complex-mediated inflammatory glomerulonephritis.

(4) Suppression of Urinary Excretion of Protein and Albumin

Urines of the rabbits with glomerulonephritis induced as described above were collected and the levels of protein and albumin were determined, by the pyrogallol red method (Thomas et al. *J. Clin. Chem. Clin. Biochem.* (1981) 19:203–208) and by turbidimmunometry with the use of rabbit serum albumin as a standard (Vittinghus., E. et al. *Scand. J. Clon. Lab. Invert.* (1981) 41:627–632), respectively. Protein and albumin excreted into the urines were expressed as total amount excreted in 1 hour (mg/hr).

Urines collected during 24 hours until the BSA-immunization at day 0 contained a small amount of protein (0.60±0.03 mg/hr) and a trace amount of albumin (0.01±0.01 mg/hr). In the control group treated with TPM-1 after the BSA-immunization at day 7, urines during 28 hours from day 7 showed remarkable increases in the urinary protein (3.20±0.97 mg/hr) and albumin (1.39±0.53 mg/hr). In contrast, the protein and albumin levels in urines of the BSA-immunized WS-4-treated group collected within 28 hours from day 7 after the BSA-immunization were significantly lowered to 0.89±0.15 mg/hr protein and 0.02±0.01 mg/hr albumin and were the same as normal levels (0.93±0.41 mg/hr protein and 0.01±0.01 mg/hr albumin).

Thus, while the administration of the anti-IL-8 does not completely prevent the migration and infiltration of PMN into the glomeruli, the excretion of urinary protein and albumin are suppressed to normal levels.

The mean and standard error were calculated on all the parameters determined in this example. Statistical analyses were performed by using Student's t-test and $p<0.05$ was accepted as statistically significant.

I claim:

1. A method for treating glomerulonephritis, which method comprises administering to a subject in need of such treatment an antibody or antigen binding fragment thereof that inhibits the binding of IL-8 to neutrophils of the subject, whereby urinary excretion of protein and/or albumin associated with said glomerulonephritis in said subject is suppressed.

2. The method of claim 1 wherein said antibody or said fragment specifically binds IL-8 of said subject.

3. The method of claim 2 wherein the antibody is a monoclonal antibody.

4. The method of claim 3 wherein the monoclonal antibody has been prepared by available recombinant technology.

5. The method of claim 1 wherein the subject is a mammal.

6. The method of claim 5 wherein the mammal is a human.

7. The method of claim 2 wherein said antibody or said fragment neutralizes the biological activities of said IL-8.

8. The method of claim 7 wherein the antibody is WS-4 which is produced by murine hybridoma WS-4 deposited at the Bioengineering Industrial Technology Research Institute of the Agency of Industrial Science and Technology as FERMBP-5507.

* * * * *